US008129691B2

(12) United States Patent
Hu et al.

(10) Patent No.: US 8,129,691 B2
(45) Date of Patent: Mar. 6, 2012

(54) SECURITY INSPECTION DOOR (75) Inventors: Haifeng Hu, Beijing (CN); Zhiqiang Chen, Beijing (CN); Yuanjing Li, Beijing (CN); Jin Lin, Beijing (CN); Jinyu Zhang, Beijing (CN); Hua Peng, Beijing (CN); Qingjun Zhang, Beijing (CN); Zhongxia Zhang, Beijing (CN); Yangtian Zhang, Beijing (CN); Xiaoti Yin, Beijing (CN); Liwei Song, Beijing (CN)

(73) Assignee: Nuctech Company Limited, Beijing (CN)

( * ) Notice: Subject to any disclaimer, the term of this patent is extended or adjusted under 35 U.S.C. 154(b) by 366 days.

(21) Appl. No.: 12/468,194

(22) Filed: May 19, 2009

(65) Prior Publication Data

US 2009/0321638 A1 Dec. 31, 2009

(30) Foreign Application Priority Data

Jun. 27, 2008 (CN) .......................... 2008 1 0115772

(51) Int. Cl.
G01T 3/00 (2006.01)
(52) U.S. Cl. .................................. 250/390.01
(58) Field of Classification Search .............. 250/390.01 –390.12
See application file for complete search history.

(56) References Cited

U.S. PATENT DOCUMENTS

| 4,012,690 A | * | 3/1977 | Heytow | 324/243 |
| 4,586,441 A | | 5/1986 | Zekich | 109/8 |
| 5,692,029 A | | 11/1997 | Husseiny et al. | 378/88 |
| 5,915,268 A | | 6/1999 | Linker et al. | 73/23.2 |
| 6,073,499 A | | 6/2000 | Settles | 73/864.81 |
| 6,210,787 B1 | * | 4/2001 | Goto et al. | 428/301.4 |
| 6,742,301 B1 | | 6/2004 | Schwarz | 49/42 |
| 2001/0049926 A1 | | 12/2001 | Davies | 55/385.2 |
| 2006/0028494 A1 | | 2/2006 | De Zwart et al. | 345/691 |
| 2006/0061450 A1 | | 3/2006 | Tibi et al. | 340/5.7 |
| 2006/0255798 A1 | * | 11/2006 | Crowley et al. | 324/300 |
| 2007/0053137 A1 | * | 3/2007 | Fu et al. | 361/302 |

(Continued)

FOREIGN PATENT DOCUMENTS

CN 2591645 Y 10/2003

(Continued)

OTHER PUBLICATIONS

Kozlovsky et al., "Development of a combined device for the detection of unauthorized transportation of explosive, fissionable, and radioactive materials," 2003, Nuclear Instruments and Methods in Physics Research A, vol. 505, pp. 478-481.*

(Continued)

Primary Examiner — Kiho Kim
(74) Attorney, Agent, or Firm — Westman, Champlin & Kelly, P.A.

(57) ABSTRACT

A security inspection door comprising a narcotic drug/explosive detecting subsystem, a radioactive substance detecting subsystem and a metal detecting subsystem which are provided in a tank body is disclosed, wherein electromagnetic radiation shields are respectively provided around the three detecting subsystems, so that they are isolated from one another and are not interfered with one another. The three detecting subsystems are combined together to form a novel security inspection door, so the narcotic drugs/the explosives, the radioactive substances and the dangerous metal articles can be detected at the same time. Further, electromagnetic radiation shields are respectively provided around the three detecting subsystems, so that the three detecting subsystems are isolated from one another and are not interfered with one another, and thus, the inspection reliability and the inspection accuracy are improved.

8 Claims, 6 Drawing Sheets

U.S. PATENT DOCUMENTS

| | | | |
|---|---|---|---|
| 2008/0111545 A1* | 5/2008 | Crowley | 324/234 |
| 2008/0253392 A1* | 10/2008 | Diab | 370/466 |
| 2008/0258066 A1* | 10/2008 | Chen et al. | 250/370.01 |
| 2009/0101826 A1* | 4/2009 | Frank | 250/360.1 |

FOREIGN PATENT DOCUMENTS

| | | |
|---|---|---|
| CN | 1802675 A | 7/2006 |
| CN | 1834690 A | 9/2006 |
| DE | 43 06 187 | 2/1997 |
| DE | 10 2006 036 108 | 11/2007 |
| EP | 1 286 151 A1 | 12/2001 |
| GB | 2 440 937 | 2/2008 |
| WO | WO 03 069 320 | 8/2003 |
| WO | WO 2004/097456 | 11/2004 |

OTHER PUBLICATIONS

Office Action issued in the related German patent application No. 102009003239.8-52 issued Jan. 25, 2010, 7 pages.

* cited by examiner

SECURITY INSPECTION DOOR

The present application claims priority of Chinese patent application Serial No. 200810115772.4, filed Jun. 27, 2008, the content of which is hereby incorporated by reference in its entirety.

FIELD OF THE INVENTION

The present invention relates to a security inspection door, and particularly to a security inspection door which can detect narcotic drugs/explosives, radioactive substances and dangerous metallic articles at the same time.

BACKGROUND OF THE INVENTION

Since the terror event happened on Sep. 11, 2001 in US, anti-terror has become a common topic all over the world. Also, terror events have happened in U.S.A., Russia, U.K., Egypt, Spain, Indonesia, India and the like, and U.S.A. even provoked two wars for this reason. Terrorists often start a terror attack with "human bombs", which severely threatens the security of common people and the social stability.

Generally, security doors in the market for inspecting a person, however, can only detect magnetic metals, and can not detect non-magnetic metals. Therefore, they can not detect explosives and narcotic drugs, which is a serious security loop-hole.

It is possible to detect suspicious particles of the narcotic drugs, explosives and the like carried by the person with the development of the narcotic drug/explosive detecting (IMS) technique. Recently, a great many of efforts have been made on a door-type person detecting technique using the IMS technique, and a number of patent applications, such as EP1286151A1, U.S. Pat. No. 5,915,268A1, U.S. Pat. No. 6,073,499A1 and US2001049926A1 etc. have been filed.

In those patent applications, a plurality of door structures is provided to facilitate collecting airflows; a concentration concept is employed (for example, in U.S. Pat. No. 6,073,499A1) to improve collection efficiency. And in order to blow down the suspicious particles carried on the person's clothes, various methods are used, such as a continuous airflow is blown towards the person being inspected, as described in US2001049926A1; and a jet head for air-spraying pressurized air is added later to blow the clothes, as well as the setting of the airflow and the direction of the jet head, for example, upward or downward, as described in EP1286151A1, U.S. Pat. No. 5,915,268A1, and U.S. Pat. No. 6,073,499A1.

In order to detect special nucleus substances and radioactive substances, Chinese patent CN02289581.4 proposes a door-type γ radioactivity security inspecting device in which NaI (TI) scintillating medium for measuring the γ radioactivity are shielded directionally so that only the γ radioactivity in a spatial angle range at one side of the scintillating medium can be detected; and a plurality of γ probes are arranged in doorposts at two sides of a doorframe to improve efficiency of detecting the radioactive substances. US2006/028494A1 also provides a radioactive security inspection door in which a plurality of detectors and a collimator array are applied to achieve the function of detecting the γ and n simultaneously.

In the aspect of metal detecting, Chinese patent CN1834690 provides a pass-through metal detecting system, in which a double transmitting and a double receiving antenna and corresponding circuits and software are used to improve the defect that the magnetic field is not distributed uniformly, and thus the ability of metals detection is improved. Chinese patent CN1802675A (WO2004/097456) provides a metal detector with a portable structure, and the metal detector may operate for a long time by means of battery or an AC power supply by setting a heavy load cycle working mode and an impulse working mode.

However, for various reasons, a detecting device, which can detect the narcotic drugs/the explosives, the radioactive substances and the dangerous metal articles at the same time, can not be founded in the market.

SUMMARY OF THE INVENTION

The present invention is directed to provide a security inspection device which can detect the narcotic drugs/the explosives, the radioactive substances and the dangerous metal articles at the same time.

One aspect of this invention is to provide a security inspection door which can detect the narcotic drugs/the explosives, the radioactive substances and the dangerous metal articles at the same time, comprising a narcotic drug/explosive detecting subsystem, a radioactive substance detecting subsystem and a metal detecting subsystem provided in a tank body, wherein electromagnetic radiation shields are provided respectively around the three detecting subsystems, so that the narcotic drug/explosive detecting subsystem, the radioactive substance detecting subsystem and the metal detecting subsystem are isolated from one another and are not interfered with one another.

In the present invention, the narcotic drug/explosive detecting subsystem, the radioactive substance detecting subsystem and the metal detecting subsystem are combined together for the first time to form a novel security inspection door, so the narcotic drugs/the explosives, the radioactive substances and the dangerous metal articles can be detected at the same time.

With the present invention, the detecting of the narcotic drugs/the explosives, the specific nucleus substances/the radioactive substances and the prohibited metal articles is carried out in one single inspection, such that the security of persons and facilities at an important occasion is ensured. Further, in the present invention, electromagnetic radiation shields are provided respectively around the three detecting subsystems, so that the narcotic drug/explosive detecting subsystem, the radioactive substance detecting subsystem and the metal detecting subsystem are isolated from one another and are not interfered with one another, and thus, inspection reliability and inspection accuracy thereof are improved.

DETAILED DESCRIPTION OF EMBODIMENTS OF THE INVENTION

Figure 1:
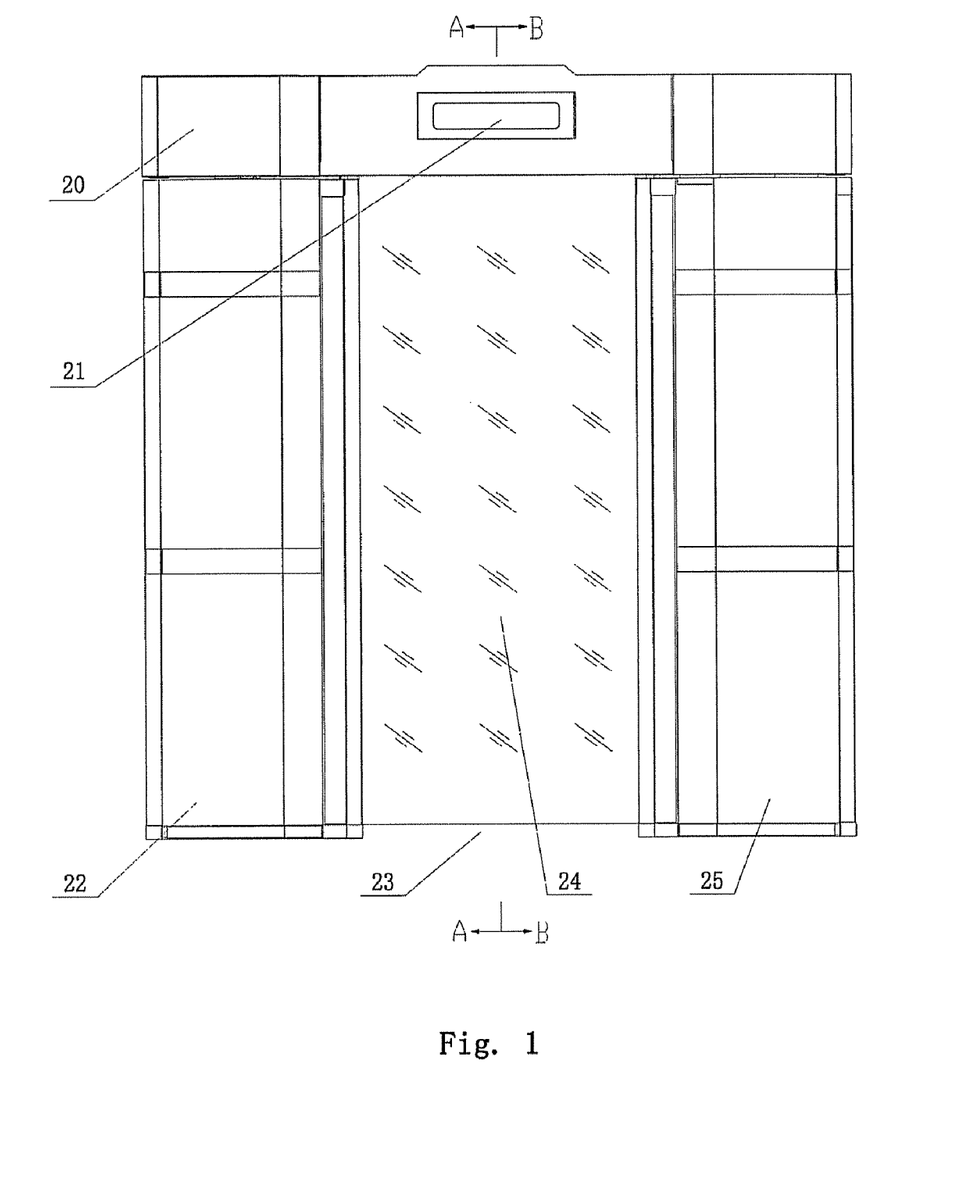
FIG. 1 is a front view of a security inspection door according to one embodiment of the present invention.
Figure 2:
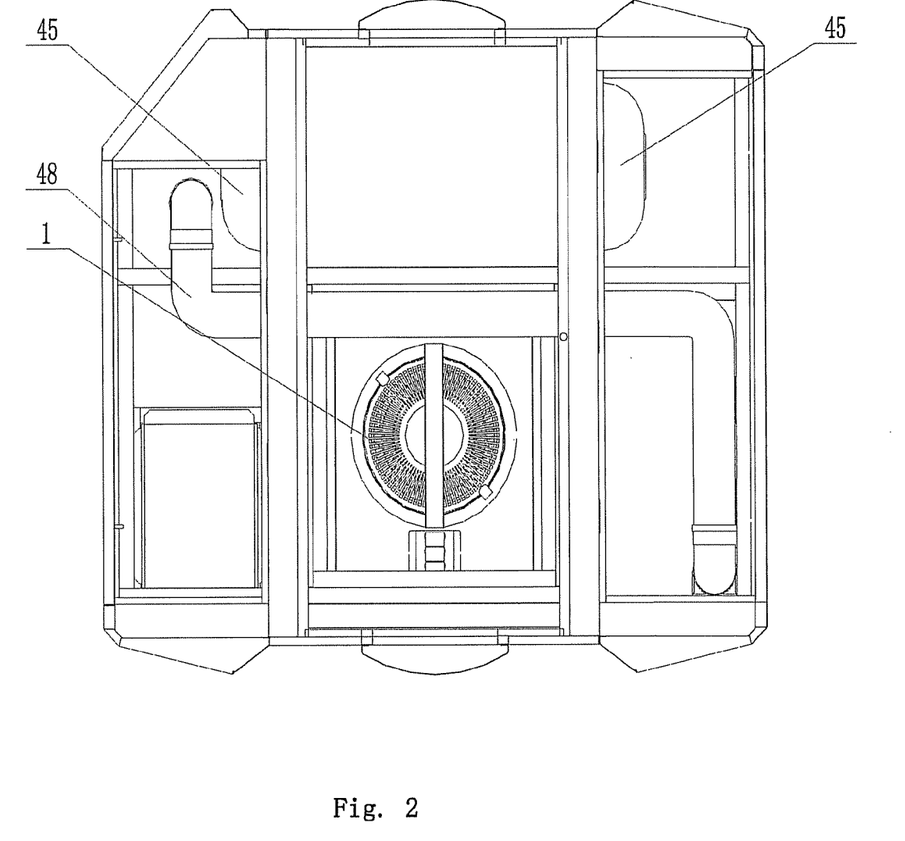
FIG. 2 is a top view of the security inspection door according to one embodiment of the present invention.
Figure 3:
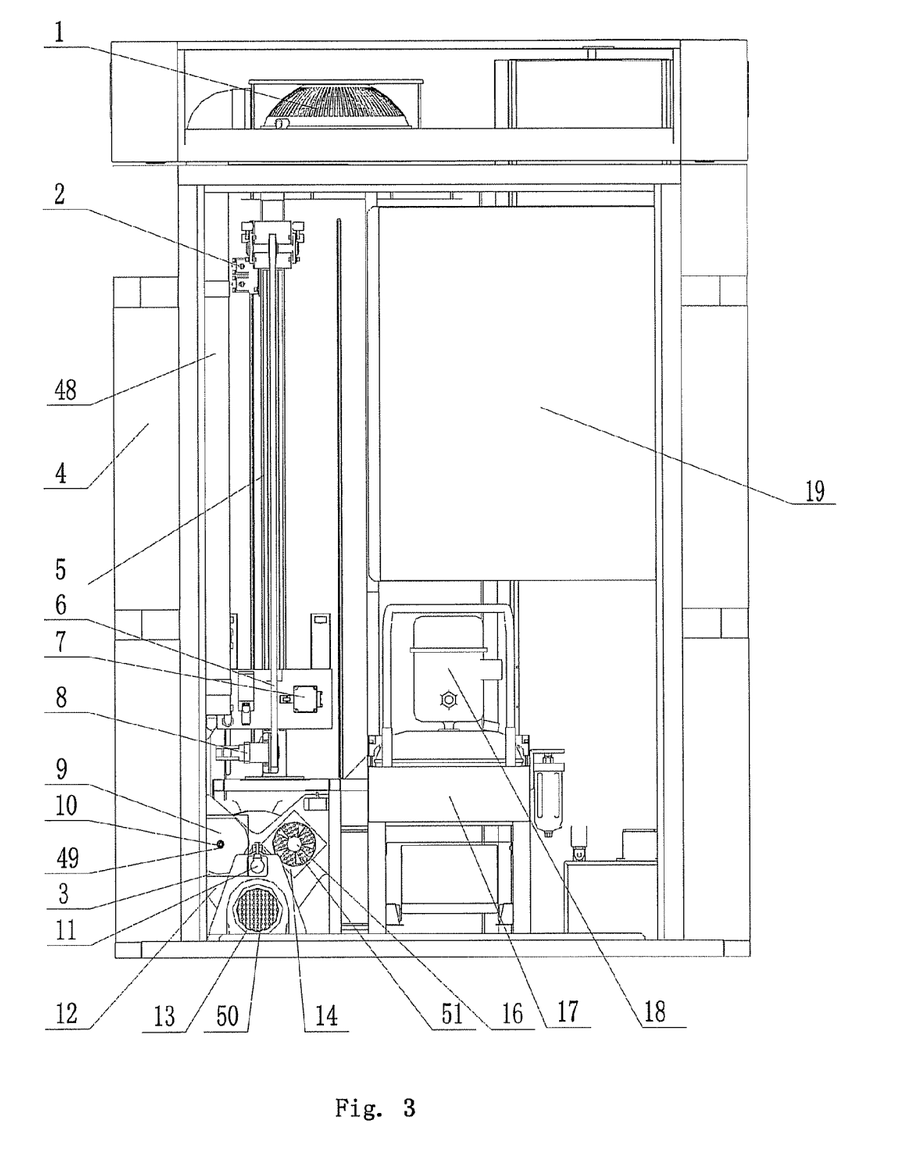
FIG. 3 is a right side view of the security inspection door according to one embodiment of the present invention.
Figure 4:
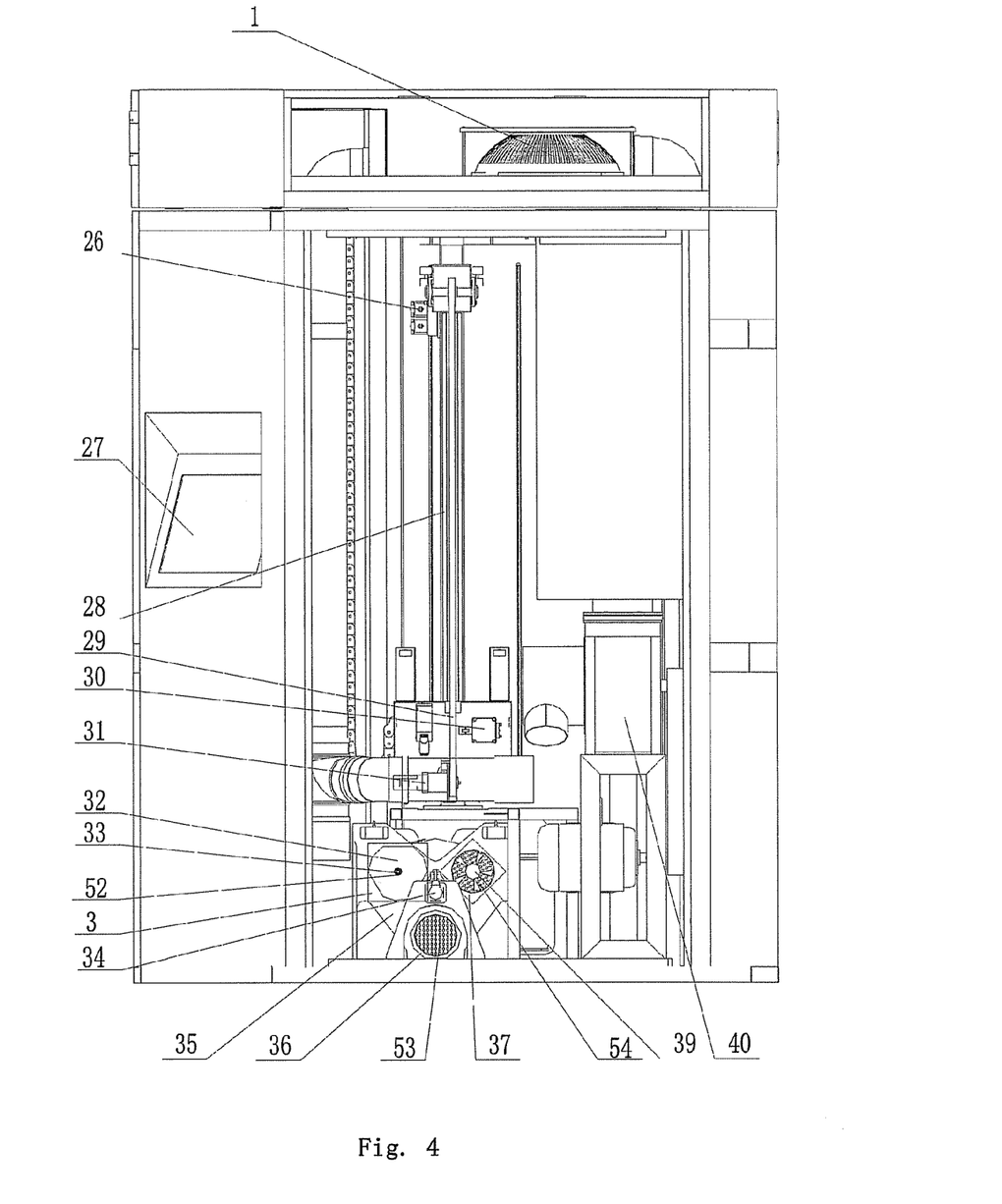
FIG. 4 is a left side view of the security inspection door according to one embodiment of the present invention.
Figure 5:
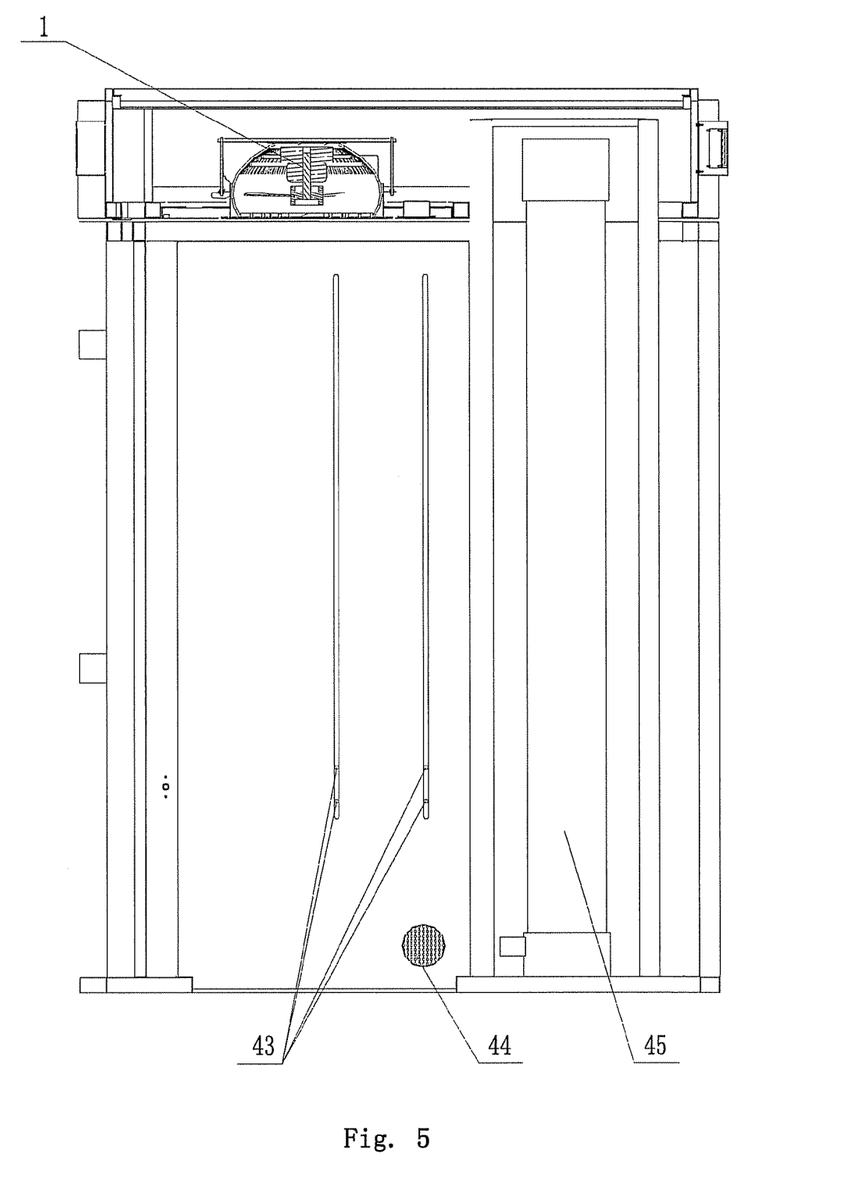
FIG. 5 is a view seen from A-A direction in FIG. 1.
Figure 6:
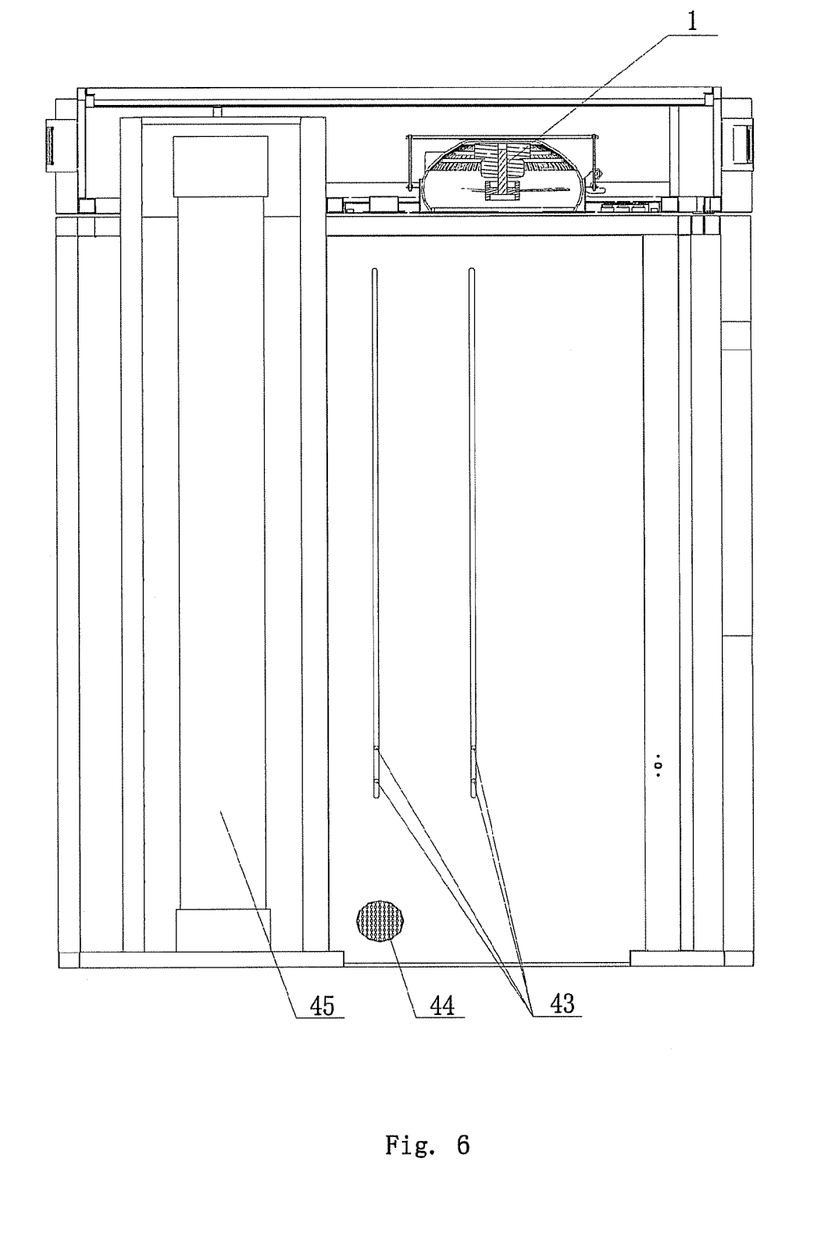
FIG. 6 is a view seen from B-B direction in FIG. 1.

FIG. 1 is a front view of a security inspection door according to one embodiment of the present invention. FIG. 2 is a top view of the security inspection door according to one embodiment of the present invention. FIG. 3 is a right side view of the security inspection door according to one embodiment of the present invention. FIG. 4 is a left side view of the security inspection door according to one embodiment of the present invention. FIG. 5 is a view seen from A-A direction in FIG. 1. FIG. 6 is a view seen from B-B direction in FIG. 1.

As shown in FIG. 1, the security inspection door comprises a left tank body 22, a right tank body 25 and a top tank body 20 which form a door-shaped inspection passage 23. Preferably, a glass door 24 is provided at an entrance and/or an exit of the door-shaped passage 23, and when a person enters the inspection passage, the glass door 24 may be closed so that an inner space of the passage is isolated from outside, thus an ambient interference can be prevented and inspection accuracy is improved.

In the present embodiment, the left tank body 22, the right tank body 25 and the top tank body 20 are made of metal sheets, so that an electromagnetic radiation shielding space is formed inside the left tank body 22, the right tank body 25 and the top tank body 20. A narcotic drug/explosive detecting subsystem, a radioactive substance detecting subsystem and a metal detecting subsystem of the security inspection door are arranged in the electromagnetic radiation shielding space formed by these tank bodies, in this way, the narcotic drug/explosive detecting subsystem, the radioactive substance detecting subsystem and the metal detecting subsystem are partially prevented from being affected by electromagnetic radiations outside the tank bodies. Preferably, a space accommodating the narcotic drug/explosive detecting subsystem, a space accommodating the radioactive substance detecting subsystem, and a space accommodating the metal detecting subsystem are isolated from one another, thus electromagnetic radiation interference among the narcotic drug/explosive detecting subsystem, the radioactive substance detecting subsystem and the metal detecting subsystem is partially prevented.

As shown in FIGS. 2, 3 and 4, the narcotic drug/explosive detecting subsystem comprises an air supply device, a group of air-spraying devices provided in the right tank body 25, another group of air-spraying devices provided in the left tank body 22, a set of detecting devices provided in the right tank body 25, another set of detecting device provided in the left tank body 22 and a fan 1 provided in the top tank body 20.

Specifically, as shown in FIGS. 3 and 4, the air supply device comprises an air container 18, an air compressor 17 and an air path 48.

Specifically, as shown in FIGS. 3 and 6, the internal construction of the right tank body 25 is shown. The group of air-spraying devices in the right tank body 25 comprises an upper limit switch 2, a lifting guide rail 5, a synchronously lifting strip 6 for the group of air-spraying devices, a high speed solenoid valve/rotating motor 7, a lifting motor 8 for the air-spraying devices, and nozzles 43.

Specifically, as shown in FIGS. 3 and 5, the internal construction of the left tank body 22 is shown. The another group of air-spraying devices in the left tank body 22 comprises an upper limit switch 26, a lifting guide rail 28, a synchronously lifting strip 29 for the another group of air-spraying devices, a high speed solenoid valve/rotating motor 30, a lifting motor 31 for the air-spraying devices, and nozzles 43.

Specifically, as shown in FIGS. 3 and 4, the group of detecting devices in the right tank body 25 comprises a narcotic drug/explosive detector (IMS) 3, a filter screen heater 9, a filter screen rotary table motor 11, a filter screen rotary table mechanism 12, a cleaning axial blower 16, and filter screens 49, 50 and 51.

Specifically, the another group of detecting devices in the left tank body 22 comprises a narcotic drug/explosive detector (IMS) 55, a filter screen heater 32, a filter screen rotary table motor 34, a filter screen rotary table mechanism 35, a cleaning axial blower 39, a centrifugal blower 40, and filter screens 52, 53 and 54.

Since the air compressor 17 producing interfering electromagnetic waves is provided in the air supply device, a metal shielding housing is provided around the air supply device to form an electromagnetic radiation shielding so as to prevent the radioactive substance detecting subsystem and the metal detecting subsystem from being affected by the electromagnetic waves produced by the air compressor 17.

In a similar way, since the solenoid valve 7 producing interfering electromagnetic waves is provided in the air-spraying devices, a metal shielding housing is provided around the air-spraying devices to form an electromagnetic radiation shielding so as to prevent the radioactive substance detecting subsystem and the metal detecting subsystem from being affected by the electromagnetic waves produced by the solenoid valve 7.

In a similar way, since the blowers 39, 40 producing interfering electromagnetic waves are provided in the detecting devices, metal shielding housings are provided around the detecting devices to form electromagnetic radiation shields so as to prevent the radioactive substance detecting subsystem and the metal detecting subsystem from being affected by the electromagnetic waves produced by the blowers 39, 40.

In a similar way, since the fan 1 produces interfering electromagnetic waves, a metal shielding housing is provided around the fan 1 to form an electromagnetic radiation shield, preventing the radioactive substance detecting subsystem and the metal detecting subsystem from being affected by the electromagnetic waves produced by the fan 1.

It is noted that in the preferred embodiment of the present invention, both the left tank body 22 and the right tank body 25 comprise therein a group of air-spraying devices and a group of detecting devices, however, a group of air-spraying devices and a group of detecting devices may be provided only in the left tank body 22 or the right tank body 25, and such modification shall fall within the scope of the present invention.

As shown in FIGS. 3 and 4, the air-spraying devices in the right and left tank bodies 25 and 22 may move up and down along the lifting guide rail 5, and the nozzles 43 on the air-spraying devices are moved together with the air-spraying devices.

As shown in FIGS. 5 and 6, two rows of the nozzles 43 are arranged on inner side walls of the right and left tank bodies 25 and 22 respectively, and each row includes two nozzles 43. The high speed solenoid valve/rotating motor 7 controls the pressurized impulse airflow jetted from the nozzles 43. Each row of the nozzles 43 is directed towards a center of the inspection passage 23, and the nozzles 43 move from above to bottom along guide grooves in the right and left tank bodies 25 and 22 so as to continuously move the impulse airflow to jet towards the person being inspected. It is noted that one or three or more rows of nozzles may be provided on the inner side walls of the right and left tank bodies 25 and 22 respectively, and the number of the nozzles 43 in each row is not limited to two, and it may be one or three or more.

As shown in FIG. 3, the radioactive substance detecting subsystem comprises a set of ray detecting devices 4 provided in the left tank body 22 and a set of ray detecting devices 4 provided in the right tank body 25. Metal shielding housings are provided around the ray detecting devices 4 to form electromagnetic radiation shields, so that the interference of outside electromagnetic radiations are prevented. It is noted that a set of ray detecting devices 4 may be provided only in the left tank body 22 or the right tank body 25, and such modification should be fallen within the scope of the present invention.

Further, as shown in FIG. 3, the ray detecting devices 4 are provided at a substantially middle position in a height direction of the left tank body or the right tank body, so that the height at which the ray detecting devices 4 are provided substantially corresponds to a half of the body height of the person. In this way, an effective detecting range of the ray detecting devices 4 may cover the whole body height of the person.

Further, although it is not shown in the Figs., the ray detecting devices 4 comprise γ detectors and n (neutron) detectors which are arranged alternatively.

As shown in FIGS. 2, 5 and 6, the metal detecting subsystem comprises a set of metal detecting devices 45 provided in the left tank body 22 and a set of metal detecting devices 45 provided in the right tank body 25, metal shielding housings are provided around the metal detecting devices 45 to form electromagnetic radiation shields so as to prevent the interference of the outside electromagnetic radiations. It is noted that a set of metal detecting devices 45 may be provided only in the left tank body 22 or the right tank body 25, and such modification should be fallen within the scope of the present invention.

Moreover, although it is not shown in the Figs., signal isolators are provided respectively on signal lines, power supply lines and ground lines of above three detecting subsystems so as to prevent signal cross fires among the three detecting subsystems. Specifically, electric wave filters, decoupling devices and optoelectronic isolators are provided on the signal lines, the power supply lines and the ground lines. Preferably, the signal lines of the three detecting subsystems are separated in space from one another, and a vertical cross wiring is used in the case that a cross wiring is needed.

Operating Principle of the Present Invention

1. Operating Principle of the Narcotic Drug/Explosive Detecting Subsystem

FIG. 1 shows the appearance of the security inspection door for inspecting the narcotic drugs, the explosives, the radioactive substances and the metal substances. Indicating lights 21 are used to indicate states in which the person being inspected is: an inspecting state (a yellow light), an idle state (a green light), and an alarming state (a red light).

As shown in FIG. 3, the air compressor 17 supplies pressurized air which is provided to the nozzles 43 by air inlet pipes, and the airflows jetted from each group of nozzles 43 are controlled by the high speed solenoid valve/rotating motor 7. The nozzles 43 are mounted on the air-spraying devices and are moved up and down along the lifting guide rail 28 when the air-spraying devices are driven by the lifting motor 31 for the air-spraying devices through the synchronously lifting strip 29. With an electric control screen, a touching screen/computer system 27 controls members, such as the lifting motor 31 for the air-spraying devices, the high speed solenoid valve/rotating motor 7, the air compressor 17, the centrifugal blower 40, the fan 1.

The nozzles 43 are mounted on the air-spraying devices in the left tank body 22 and the right tank body 25 respectively, as shown in FIGS. 5 and 6. The pressurized impulse airflows jetted from the nozzles 43 are controlled by the high speed solenoid valve/rotating motor 7. Each group of the nozzles 43 is directed towards the center of the inspection passage 23, and the nozzles 43 are moved from above to bottom along the guide grooves in the right and left tank bodies 25 and 22 so as to continuously move the impulse airflows jetted towards the person being inspected.

The fan 1 is mounted at a middle portion of the top tank body 20, and provides a downward airflow during operating, so that the particles blown down from the person are blown to a lower portion of the inspection passage 23. A collecting passage 44 is provided at lower portions of the left tank body 22 and the right tank body 25, into which the particles are sucked by the centrifugal blower 40. Filter screens 49 and 52 are mounted at the end of the collecting passage 44, which collect the particles blown down from the person.

The filter screens 49, 50, 51, 52, 53 and 54 are respectively mounted on the filter screen turntables 12, 35, which are controlled to turn by the filter screen turntable motors 11, 34. Each filter screen operates at different stations, alternatively. There are three stations on the filter screen turntables 12, 35, respectively, that is, filter screen detecting stations 10, 33, collecting stations 13, 16, and filter screen cleaning stations 14, 37. The filter screen detecting stations 10, 33 respectively comprise the filter screen heaters 9, 32, and the narcotic drug/explosive detectors (IMS) 3, 55, and are used to detect the particles absorbed on the filter screens. The filter screen cleaning stations 14, 37 are respectively mounted with the cleaning axial blowers 16, 39, and are used to clean the filter screens.

The glass door 24 is optionally mounted on two sides of the inspection passage 23 based on actual demands.

When the inspection is started, the indicating lights 21 indicate the idle state (the green light is on), and the person to be inspected enters the inspection passage 23 and stands at a designated position; then the system begins to jet and blow air and to collect the particles blown down from the person; after the completion of the collecting, the filter screens at the collecting stations 13, 36 are turned by the filter screen turntable motors 11, 34 on the filter screen turntables 12, 35 to the screen detecting stations 10, 33 to perform the detection; the filter screen heaters 9, 32 at the filter screen detecting stations 10, 33 heat the filter screens, and after being gasified, the particles absorbed on the filter screens are sucked into the narcotic drug/explosive detectors 3, 55 so as to be analyzed, the analysis result is transmitted to the touching screen/computer system 27 for further processing, and is displayed on the screen. If narcotic drug/explosive traces are found, a warning is sent out while the indicating lights 21 are alarmed (the red light is on); if no suspicious articles are found, the current inspection is completed, and the indicating lights 21 turn to the idle state (the green light is on) to wait for the next inspection.

2. Operating Principle of the Radioactive Substance Detecting Subsystem

The person to be inspected enters the designated position in the inspection passage 23. The narcotic drug/explosive detecting subsystem begins to operate prior to the operating of the narcotic drug/explosive detecting subsystem; and after the narcotic drug/explosive detecting subsystem completes its current detection, the radioactive substance detecting subsystem completes its current detection.

The γ ray and the n ray are detected by the radioactive substance detector 4, and the detected signals are analyzed. Detecting data are finally transmitted to the touching screen/computer system 27 for further processing and displaying. If radioactive substances are detected, the system will raise the alarm signal.

3. Operating Principle of the Metal Detecting Subsystem

The metal detector 45 is installed as shown in FIGS. 2, 5 and 6. When the person being inspected goes through the inspection passage 23, the metal detector 45 performs detecting, and the results of the detecting are transmitted in a communicating manner to the touching screen/computer system 27 for further processing and displaying. And the sensitivity of the metal detector 45 may be set according to actual demands.

In conclusion, the three detecting subsystems with different functions are combined together to complete the task of inspections of the narcotic drugs/explosives, the radioactive substances and the prohibited metal articles at the same time, so the inspecting efficiency is improved.

Although exemplary embodiments have been shown and described, it would be appreciated by those skilled in the art that various changes or modifications may be made in these embodiments without departing from the principles and spirit of the present invention, the scope of which is defined in the claims and their equivalents.

What is claimed is:

1. A security inspection door, comprising a narcotic drug/explosive detecting subsystem, a radioactive substance detecting subsystem and a metal detecting subsystem which are provided in a tank body, wherein electromagnetic radiation shields are respectively provided around the three detecting subsystems, so that the narcotic drug/explosive detecting subsystem, the radioactive substance detecting subsystem and the metal detecting subsystem are isolated from one another and are not interfered with one another, wherein the tank body comprises a left tank body, a right tank body and a top tank body defining a door-shaped inspection passage, and said left tank body, said right tank body and said top tank body are made of metal to form electromagnetic radiation shields, and wherein the narcotic drug/explosive detecting subsystem comprises:
at least one group of air-spraying devices provided in the right tank body and/or the left tank body and be movable up and down in a vertical direction;
a set of air supply devices for supplying air to the air-spraying devices;
at least one group of detecting devices provided in the right tank body and/or the left tank body; and
a fan provided in the top tank body, wherein metal shielding housings are respectively provided around the air supply devices, the air-spraying devices, the detecting devices and the fan so as to form electromagnetic radiation shields.

2. The security inspection door according to claim 1, wherein
a group of the air-spraying devices is respectively provided in the left tank body and the right tank body; and
a group of detecting devices is provided in the left tank body and the right tank body respectively.

3. The security inspection door according to claim 1, wherein the radioactive substance detecting subsystem comprises at least one set of ray detecting devices provided in the right tank body and/or the left tank body, and metal shielding housings are provided around the ray detecting devices to form electromagnetic radiation shields.

4. The security inspection door according to claim 3, wherein:
a set of the ray detecting devices is respectively provided in the left tank body and the right tank body; and
each set of the ray detecting devices comprises γ detectors and n (neutron) detectors which are arranged alternatively.

5. The security inspection door according to claim 3, wherein
the ray detecting devices are provided at a substantially middle position in a vertical direction of the left tank body or the right tank body, so that the height at which the ray detecting devices are provided substantially corresponds to a half of the body height of a person.

6. The security inspection door according to claim 1, wherein
the metal detecting subsystem comprises at least one set of metal detecting devices provided in the right tank body and/or the left tank body, and metal shielding housings are provided around the metal detecting devices so as to form electromagnetic radiation shields.

7. The security inspection door according to claim 6, wherein
a set of metal detecting devices is respectively provided in the left tank body and the right tank body.

8. The security inspection door according to claim 1, wherein
electric wave filters, decoupling devices and optoelectronic isolators are respectively provided on signal lines, power supply lines and ground lines of the three detecting subsystems; and
said signal lines of the three detecting subsystems are separated from one another in space, and a vertical cross wiring is employed in the case that a cross wiring is needed.

* * * * *